United States Patent [19]

Gardella et al.

[11] 4,002,718

[45] Jan. 11, 1977

[54] GELATIN-ENCAPSULATED DIGOXIN SOLUTIONS AND METHOD OF PREPARING THE SAME

[75] Inventors: Libero A. Gardella, Libertyville; Helen Kesler, Barrington, both of Ill.

[73] Assignee: Arnar-Stone Laboratories, Inc., Mount Prospect, Ill.

[22] Filed: Oct. 16, 1974

[21] Appl. No.: 515,087

[52] U.S. Cl. .............................. 424/37; 424/182; 206/524.7

[51] Int. Cl.² ..................... A61J 3/07; A61K 9/48; A61K 31/705

[58] Field of Search ............... 424/37, 182; 206/84

[56] References Cited

UNITED STATES PATENTS

| | | | |
|---|---|---|---|
| 2,298,122 | 10/1942 | Hailer et al. | 424/37 |
| 2,415,312 | 2/1947 | Thompson et al. | 424/182 |
| 2,698,822 | 1/1955 | Halpern et al. | 424/182 |
| 2,765,256 | 10/1956 | Beals et al. | 424/182 |
| 2,780,355 | 2/1957 | Palermo et al. | 206/84 |
| 2,860,086 | 11/1958 | Stoll et al. | 424/182 |
| 2,889,252 | 6/1959 | Valentine et al. | 424/37 |
| 2,899,361 | 8/1959 | McMillion | 424/37 |
| 3,139,383 | 6/1964 | Neville | 424/37 |
| 3,632,742 | 1/1972 | Eckert et al. | 424/37 |
| 3,784,684 | 1/1974 | Bossert et al. | 424/37 |
| 3,867,521 | 2/1975 | Miskel et al. | 424/37 |

FOREIGN PATENTS OR APPLICATIONS

| | | |
|---|---|---|
| 817,757 | 11/1974 | Belgium |

OTHER PUBLICATIONS

Hom et al. J. Pharm. Sci. 59(6):827–830 June 1970 Oral Dosage Form Design and Its Influence on Dissolution Rates for a Series of Drugs.
Shaw et al. Lancet pp. 303–307 Aug. 12, 1972 Variation in the Biological Availability of Digoxin.
Huffman et al. Jama 222(8):957–960 Absorption of Orally Given Digoxin Preparations.
Lindenbaum Pharmacol. Rev. 25(2):229–237 June 1973 Bioavailability of Digoxin Tablets.
Huffman et al. Chem. Abst. 78 No. 37853s (1973) "Absorption of Orally Given Digoxin Preparations."
Lindenbaum et al. Chem. Abst. 79 No. 45722j (1973) "Correlation of Digoxin–Tablet Dissolution Rate with Biological Availability."
Lindenbaum Chem. Abst. 79 No. 111791j (1973) "Bioavailability of Digoxin Tablets."
Fincher J. Pharm. Sci. 57(11):1825–1835 Nov. 1968 "Particle Size of Drugs and its Relationship to Absorption and Activity."
Haleblian et al. J. Pharm. Sci. 58(8):911–929 Aug. 1969 "Pharmaceutical Applications of Polymorphism."

*Primary Examiner*—Shep K. Rose
*Attorney, Agent, or Firm*—Tilton, Fallon, Lungmus, Chestnut & Hill

[57] ABSTRACT

Digoxin solutions are disclosed which are compatible with gelatin and which are of relatively high concentration, thereby permitting encapsulation of therapeutic amounts of digoxin in soft gelatin capsules of moderate size. The digoxin is first micronized and then dissolved in a vehicle consisting predominately of polyethylene glycol having a molecular weight no greater than about one thousand and having a melting temperature no greater than about 35° C., to provide a digoxin concentration of at least one-half milligram per milliliter and preferably one milligram per milliliter. Solutions composed of various solvent blends are disclosed, including solutions which are highly viscous (semi-solid) at room temperature.

21 Claims, 2 Drawing Figures

GELATIN-ENCAPSULATED DIGOXIN SOLUTIONS AND METHOD OF PREPARING THE SAME

BACKGROUND

Digoxin is a cardiac glycoside known for use in the treatment of congestive heart failure and, when administered at the proper therapeutic dosage level, exerts a direct cardiotonic action on the myocardium to increase the force of contraction and improve cardiac tone. While the proper dosage level may vary considerably from patient to patient, the therapeutic dosage range is nevertheless quite low when compared with most other drugs. Moreover, the ratio between toxic and effective doses may also be relatively low. For example, it has been reported that a 50 percent change in the steady-state plasma concentration of digoxin may bring a patient into either the subtherapeutic or toxic concentration range. G. Levy et al, Circulation, Vol. 49, pp. 391–394, March 1974. The need to assure the adequate bioavailability of digoxin products is therefore readily apparent.

A further clinical problem arises because a digoxin tablet may contain a correct dose of the drug but provide only a portion of that dose for absorption by the patient. Incomplete absorption occurs if a digoxin tablet dissolves relatively slowly in the gastrointestinal fluids, and it has been found that the dissolution rate of digoxin tablets varies considerably from brand to brand and (for the same brand) from batch to batch. Such variations in dissolution rate lead to marked differences in the plasma digoxin levels and clinical response achieved during maintenance digoxin therapy. T. R. D. Shaw, American Heart Journal, Vol. 87, No. 3, pp. 399–401, March 1974.

The problem is still further complicated by the relatively low dosage of tablet formulations (a typical tablet dosage falls within the range of 0.125 to 0.5 milligrams) since even slight variations in the distribution of digoxin during a tableting operation may result in significant differences in the dosage levels of digoxin in the same batch or successive batches of tablets.

While it is known that when digoxin is administered orally as a solution absorption is nearly complete, users commonly reject liquid preparations in favor of tablets because of the far greater convenience in carrying, storing, and administering the drug in solid form. Therefore, despite the variations in bioavailability and therapeutic response of digoxin in the solid state, and indications of poor content uniformity from tablet to tablet and/or lot to lot, tablet formulations of digoxin constitute the primary form in which the drug is marketed and used.

While it might be thought that an encapsulated form of digoxin in solution might overcome the aforementioned problems, digoxin is insoluble in water and is known to be soluble only in solutions (such as dilute alcohol) which also dissolve gelatin capsules. Consequently, the only recognized choices for preparing digoxin in therapeutic dosage form are as a solid (i.e., tablets, powders, crystals) or as a liquid to be dispensed in measured amounts from a bottle or other container.

SUMMARY OF THE INVENTION

A main aspect of this invention lies in the discovery that solutions of digoxin may indeed be prepared which are both compatible with gelatin capsules (i.e., will not dissolve such capsules) and of sufficient concentration (at least one-half milligram per milliliter, and preferably one milligram per milliliter) to provide a therapeutic dose in a capsule of moderate size. A further aspect lies in the discovery that a digoxin solution having such characteristics may be prepared which, in addition, is a semi-solid at room temperature. Consequently, such a semi-solid solution would not be apt to leak from a gelatin capsule at normal handling and storage temperatures. The result is gelatinencapsulated digoxin solutions which provide the advantages of a dosage form which is in solution but which can be taken with the convenience of a tablet without the problems of uniformity and dissolution rate associated with tablets and other prior solid dosage forms.

The gelatin-compatible digoxin solutions of this invention are characterized by a solvent consisting predominantly of polyethylene glycol. In general, the polyethylene glycol has a molecular weight no greater than about one thousand and may be blended with a relatively small proportion of glycerin, propylene glycol, polyvinyl pyrrolidone, or the like, to promote dissolution of the digoxin without softening or dissolving the gelatin casing of the capsule. Although the vehicle may be a semi-solid (or solid) at room temperature, it must have a melting temperature no greater than about 35° C. Most desirably, the polyethylene glycol solvent is blended with a minor proportion of relatively high molecular weight polyethylene glycol to produce a thixotropic solution which may easily be encapsulated (as a liquid at slightly above room temperature) in soft gelatin capsules and which is virtually incapable of leaking from those capsules when such capsules are later stored under dry conditions at room temperature or below.

While it is recognized that polyethylene glycol is a common solvent in the preparation of encapsulated drug solutions, it is to be noted that digoxin was not previously known to be soluble in liquid low molecular weight polyethylene glycol and is in fact virtually insoluble in its commercially available form in that solvent. Therefore, a further aspect of this invention lies in the discovery that digoxin is capable of being dissolved in a solvent consisting predominantly of low molecular weight (no greater than 1000) polyethylene glycol only if the digoxin is first micronized, that is, reduced to an average particle size of 10 microns or less, with a maximum particle size no greater than approximately 60 microns. The reasons for the substantial increase in solubility of digoxin in such polyethylene glycol solvents may not be fully understood at this time but it is believed that micronization results in a different crystalline structure of greater solubility. Otherwise micronization would be expected only to increase the dissolution rate of the digoxin without significantly altering its solubility, whereas in fact such micronization greatly increases the ultimate extent of such solubility.

Other advantages and objects of the invention will become apparent as the specification proceeds.

DRAWINGS

DETAILED DESCRIPTION

Figure 1:
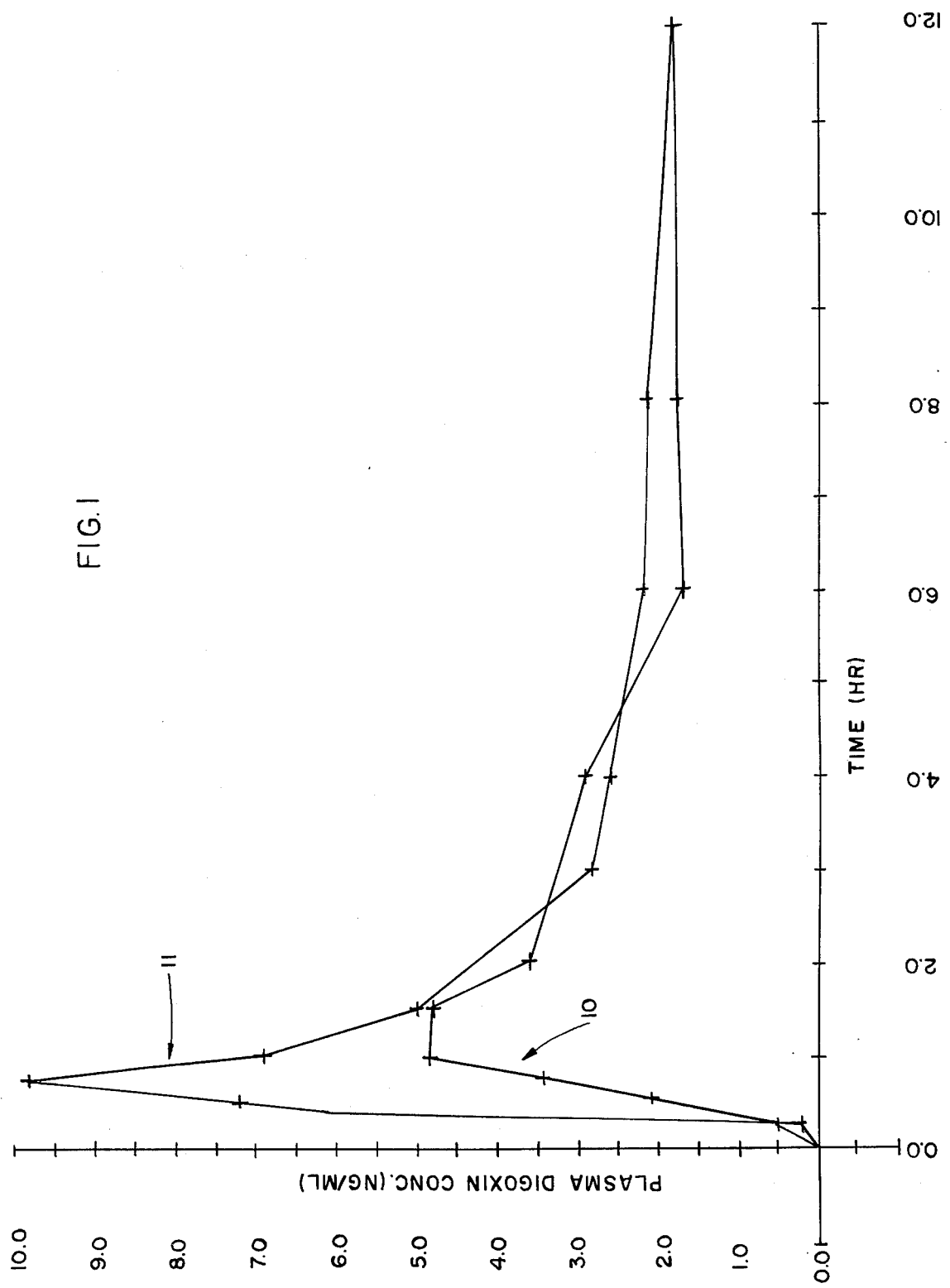
FIG. 1 is a graph illustrating the bioavailability of a digoxin solution prepared in accordance with the present invention when compared with a conventional solid form of digoxin, the dosage amounts for both preparations being the same (0.5 milligrams of digoxin.

Micronization of digoxin (USP), the first step in the process of this invention, involves any method for reducing the solid digoxin to an average particle size of 10 microns or less. Hammer milling, ball milling, air impaction, or any commonly known comminution technique may be used for that purpose. To eliminate even a small proportion of relatively large particles (i.e., particles larger than 50 or 75 microns in size), the finely divided digoxin should be passed through a screen at least as fine as 200 mesh, and preferably 275 mesh.

The digoxin so micronized is then dissolved in a liquid carrier consisting predominately of polyethylene glycol having a molecular weight no greater than about 1000 and having a melting temperature no greater than about 35° C. Polyethylene glycol having a molecular weight substantially above that level, or blends which require heating substantially above 35° C. for liquification, cannot be sealed in standard soft gelatin capsules by conventional filling equipment without softening the capsules or producing imperfect seals and thereby tending to produce leakers. To hasten dissolution of the digoxin in the polyethylene glycol vehicle, moderate heating to temperatures within the range of 80°–90° may be employed; however, temperatures substantially above 100° C. should be avoided because of the danger of decomposing the drug. Following dissolution of the micronized digoxin at a concentration level of at least 0.5 milligrams per milliliter (mg per ml), and preferably at a concentration of 1.0 (or more) mg per ml, the solution is cooled to a temperature of 35° C. or less and is sealed in soft gelatin capsules utilizing standard (and well known) encapsulating equipment and procedures. In effect, the liquid digoxin solution is injected into a soft gelatin capsule as that capsule is being formed, the final step consisting of the sealing of the capsule at the point of fluid entry.

To hasten dissolution of the micronized digoxin in the liquid vehicle, the vehicle may contain small amounts (no more than about 20 percent, and preferably more than 15 percent, by weight) of other ingredients such as glycerin, propylene glycol, polyvinylpyrrolidone, or relatively high molecular weight polyethylene glycol. Thus, blends of low molecular weight (400) polyethylene glycol with 5 percent glycerin, or 5 percent propylene glycol or polyvinylpyrrolidone, have been found effective. A particularly effective blend consists predominately of polyethylene glycol (400) with a minor amount (under 5 percent) of high molecular weight (4000) polyethylene glycol, since such a blend is essentially thixotropic. At room temperature it is a semi-solid but, upon agitation or moderate heating (under 35° C.) it becomes a liquid. Therefore, such a blend may be easily sealed within soft gelatin capsules by means of customary filling equipment and techniques and, after the capsules have cooled, the solution becomes a semi-solid to render the capsules virtually leakproof during normal storage and handling at room temperature or below. Under such temperature conditions, even if the gelatin casing of the capsule should somehow become damaged, or an imperfection should cause a small opening to develop, the contents would remain in place.

Since the therapeutic properties of digoxin are well established, further discussion of those properties is believed unnecessary except perhaps to demonstrate the increased bioavailability of the drug when encapsulated in solution as described, in contrast to digoxin tablets commercially represented as containing the same amount of the drug (see Examples 2 and 3). A typical therapeutic dose of digoxin falls within the range of 0.125 to 0.5 mg; consequently, at the preferred concentration of 1 mg digoxin per ml solvent, a capsule containing a therapeutic dose of digoxin dissolved in accordance with this invention would not exceed 0.5 ml. In other words, because a relatively high concentration level of digoxin can be achieved by the method set forth herein, capsules of moderate size containing a full therapeutic dose in solution may be provided.

Other aspects and advantages of the invention will be apparent from the following illustrative examples:

EXAMPLE 1

Solutions of digoxin embodying this invention may be prepared by first micronizing digoxin USP to an average particle size no greater than 10 microns, then screening the drug through a 275 mesh screen to eliminate excessively large particles, and then dissolving measured amounts of the micronized digoxin in any of the following solvents, heated by a water bath to a temperature within the range of 80°–95° C. for 0.5 to 2.0 hours, until a concentration of 1 mg per ml is obtained:

a. Polyethylene Glycol-400 (95.5%):Polyethylene Glycol-4000 (4.5%)
b. Polyethylene Glycol-400 (95%):Glycerin (5%)
c. Polyethylene Glycol-400 (95%):Propylene Glycol (5%)
d. Polyethylene Glycol-400 (90%):Polyvinylpyrrolidone (5%): Glycerin (5%)
e. Polyethylene Glycol-400 (95%):Polyvinylpyrrolidone (5%)
f. Polyethylene Glycol-400 (90.5%):Polyethylene Glycol-4000 (4.5%): Polyvinylpyrrolidone (5.0%)
g. Polyethylene Glycol-400 (85.5%):Polyethylene Glycol-4000 (4.5%): Polyvinylpyrrolidone (5.0%) Glycerin (5.0%)

Vehicles (a), (f) and (g) are semi-solids at room temperature (or cooler) and for that reason have been found to resist leaking through capsule imperfections at room temperature or below. Solutions of digoxin in vehicles (b) through (e) are liquids at room temperature, and solutions of digoxin in vehicles (a), (f) and (g) are liquids at temperatures slightly above room temperature but approaching 35° C.; therefore, all digoxin solutions prepared using the vehicles listed above are easily sealed in soft gelatin capsules using standard capsule forming and filling equipment. Such solutions are fully compatible with the gelatin of such capsules, that is, such solutions do not dissolve or disintegrate such capsules.

EXAMPLE 2

FIG. 1 is a graph representing the bioavailability of digoxin administered to dogs of substantially the same weight, the dosage for each dog being the same (0.5 mg digoxin). One dose was administered in the form of a table commercially available under the brand name Lanoxin from Burroughs Wellcome & Co. (USA) Inc., Research Triangle Park, North Carolina, and the absorption curve, plotted in terms of plasma digoxin concentration in nanograms (ng) per ml against elapsed time in hours, is designated by numeral 10. Curve 11 represents the absorption of digoxin administered in encapsulated form, the specific formulation being 1 mg per ml micronized digoxin dissolved in vehicle (a) of Example 1. The substantially greater bioavailability of the drug when administered as an encapsulated solution rather than in solid table form is believed readily apparent.

EXAMPLE 3

Figure 2:
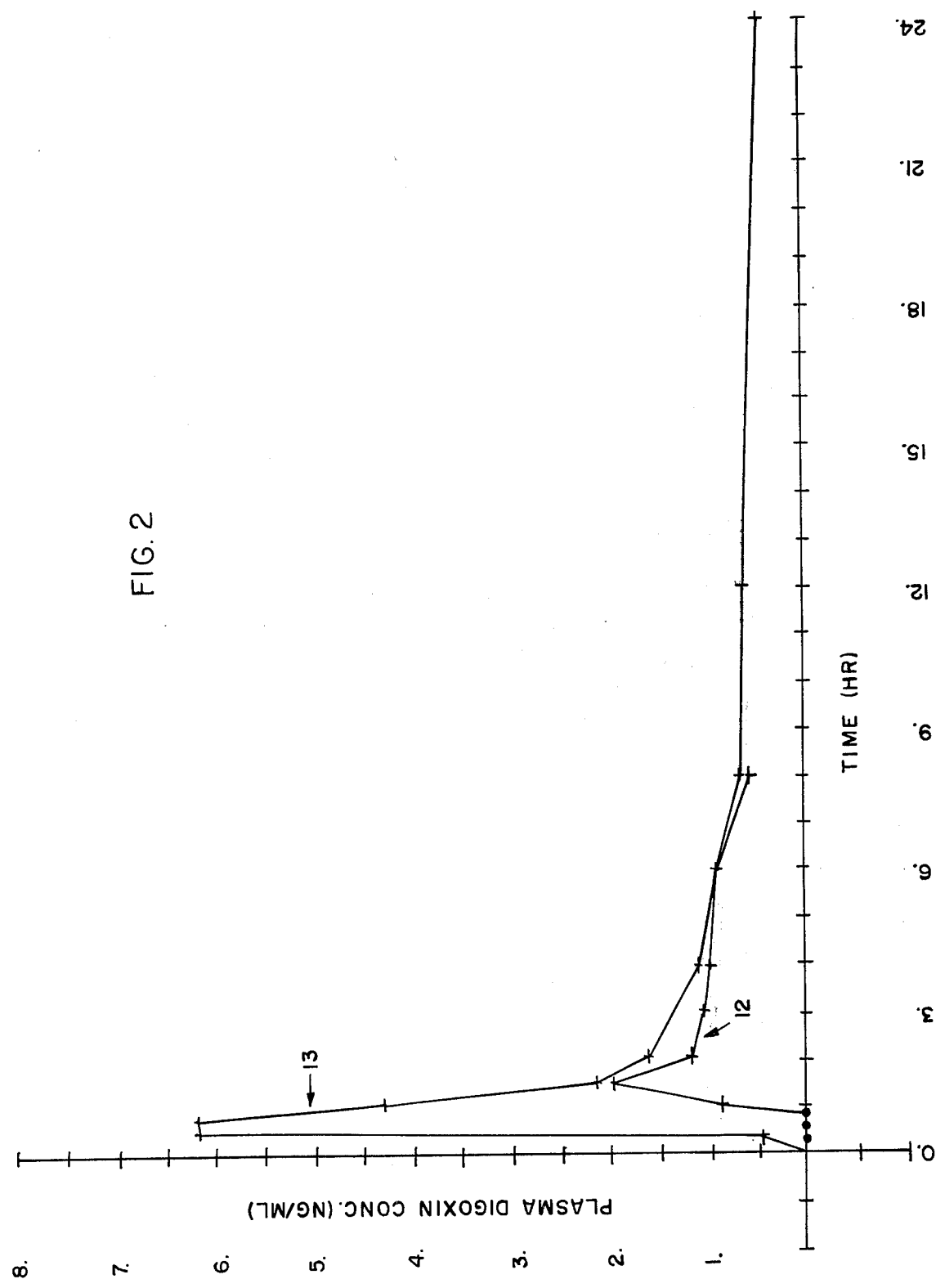
FIG. 2 is a graph similar to FIG. 1 but illustrating relative bioavailability for preparations in which the dosage is 0.25 milligrams digoxin.

FIG. 2 represents an experiment similar to that depicted in FIG. 1 except that the dosage level administered to the canine subjects was reduced to 0.25 mg digoxin. Curve 12 represents the response, measured in plasma digoxin concentration, following administration of digoxin in tablet form (Lanoxin brand). Curve 13 depicts the response when the same dosage of digoxin was orally administered in the form of an encapsulated digoxin solution of digoxin in vehicle (a) of Example 1.

EXAMPLE 4

The substantial differences in the solubilities of micronized and unmicronized digoxin in low molecular weight polyethylene glycol are illustrated by the following test using a solvent system consisting of polyethylene glycol-400 (90%), glycerin (5%), and polyvinylpyrrolidone (5%). That solvent system was selected for the solubility comparison because both polyvinylpyrrolidone and glycerin accelerate the dissolution rate of digoxin and, therefore, a solvent system containing both of those additives would be expected to be more effective than polyethylene glycol-400 alone. Also, glycerin at the 5% level would be expected to help stabilize the gelatin shell of a capsule because of the plasticizing effect of the glycerin.

The unmicronized digoxin (USP) was used in its powdered commercially-available form. The micronized digoxin was prepared as set forth in Example 1, being screened through a 275 mesh screen to eliminate excessively large particles. Samples of micronized and unmicronized digoxin were added to equal volumes of the selected vehicle and were agitated and heated in a boiling water bath for 2.0 hours. The solutions or suspensions were then allowed to set at room temperature (25° C.) for 96 hours (4 days). Calculations showed the micronized digoxin had dissolved to the extent of 1.25 mg digoxin per ml solvent. The solution was complete after the 2.0 hour heating period and the digoxin did not precipitate after cooling to room temperature.

By contrast, the unmicronized digoxin was not soluble to any appreciable extent. When subjected to the same treatment described above for dissolving the micronized digoxin (to the extent of 1.25 mg per ml), the unmicronized digoxin could not be dissolved even to the slight extent of 0.1 mg per ml.

While we have disclosed a method for preparing gelatinencapsulated liquid (or semi-liquid) solutions of digoxin at therapeutic dosage levels, including micronization of the drug prior to dissolving the same in a vehicle consisting predominately of polyethylene glycol of a molecular weight no greater than 1000 and a milling temperature not above 35° C., it is believed that such method might likewise be useful in the preparation of similar solutions of other drugs which, because of their limited solubility, have not heretofore been known or available as gelatin-encapsulated solution (liquid or semiliquid) form.

In the foregoing specification, the common therapeutic dose for digoxin has been given as 0.125 to 0.5 mg. It is to be noted, however, that such dosage is based on standard tablet formulations and, in view of the indications of greater bioavailability of the digoxin solutions of this invention, as indicated in Examples 2 and 3, a therapeutic dose of digoxin administered in a solution embodying this invention may be less than the standard dose.

In the foregoing we have disclosed embodiments of the invention in considerable detail for purposes of illustration, but it will be understood by those skilled in the art that many of these details may be varied without departing from the spirit and scope of the invention.

We claim:

1. A method for preparing digoxin in encapsulated therapeutic dosage form, comprising the steps of reducing the size of digoxin particles to an average size no larger than about 10 microns, then mixing the micronized particles of digoxin with a solvent essentially alcohol-free and consisting predominantly of polyethylene glycol of a molecular weight no greater than about 1000, and heating the mixture at a temperature below the decomposition temperature of the drug until at least 0.5 milligrams of digoxin is dissolved in each milliliter of solvent, and then encapsulating therapeutic doses of the dissolved digoxin in gelatin capsules soluble in water but insoluble in said solvent.

2. The method of claim 1 in which substantially none of said particles following said size-reducing step exceeds 75 microns in size.

3. The method of claim 1 in which said solvent consists of at least 80% by weight of polyethylene glycol having a molecular weight no greater than 1000.

4. The method of claim 3 in which said solvent also includes a minor proportion of polyethylene glycol having a molecular weight greater than 1000.

5. The method of claim 4 in which said solvent is semisolid at room temperature.

6. The method of claim 3 in which said solvent also contains a minor proportion of glycerin.

7. The method of claim 3 in which said solvent also contains a minor proportion of propylene glycol.

8. The method of claim 3 in which said solvent also contains a minor proportion of polyvinylpyrrolidone.

9. The method of claim 1 in which the material of said capsules is soft gelatin.

10. The method of claim 1 in which said digoxin is encapsulated in each of said capsules at a therapeutic dosage level of 0.125 to 0.5 milligrams.

11. The method of claim 1 in which said step of dissolving is continued until at least 1 milligram of digoxin is dissolved in each milliliter of said solvent.

12. The method of claim 1 in which said solvent has a melting temperature no greater than 35° C.

13. A digoxin preparation prepared in accordance with the method of claim 1, in which said digoxin concentration exceeds 0.5 milligrams per milliliter of solvent.

14. The preparation of claim 13 in which said solvent has a melting temperature no greater than 35° C.

15. The preparation of claim 14 in which said solvent comprises at least 80% by weight of polyethylene glycol having a molecular weight no greater than 1000.

16. The preparation of claim 15 in which said solvent also includes a minor proportion of polyethylene glycol having a molecular weight greater than 1000, said solvent being semi-solid at room temperature.

17. The preparation of claim 15 in which said solvent also contains a minor proportion of glycerin.

18. The preparation of claim 15 in which said solvent also contains a minor proportion of propylene glycol.

19. The preparation of claim 15 in which said solvent also contains a minor proportion of polyvinylpyrrolidone.

20. The preparation of claim 13 in which said digoxin concentration is at least 1 milligram per milliliter of solvent.

21. The preparation of claim 13 in which said therapeutic dose of digoxin is 0.125 to 0.5 milligrams.

* * * * *